(12) United States Patent
Kroker et al.

(10) Patent No.: US 6,998,026 B2
(45) Date of Patent: Feb. 14, 2006

(54) METHOD FOR PRODUCING TERTIARY $C_4$-$C_8$-ALKYL ESTERS OF (METH)ACRYLIC ACID

(75) Inventors: Ruprecht Kroker, Bobenheim-Roxheim (DE); Gerhard Nestler, Ludwigshafen (DE); Werner Schmitt, Frankenthal (DE); Winfried Schumm, Gelsenkirchen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 192 days.

(21) Appl. No.: 10/343,007

(22) PCT Filed: Jul. 27, 2001

(86) PCT No.: PCT/EP01/08713

§ 371 (c)(1),
(2), (4) Date: Jan. 27, 2003

(87) PCT Pub. No.: WO02/10110

PCT Pub. Date: Feb. 7, 2002

(65) Prior Publication Data

US 2003/0127315 A1 Jul. 10, 2003

(30) Foreign Application Priority Data

Jul. 28, 2000 (DE) ................. 100 36 958

(51) Int. Cl.
*B01D 1/22* (2006.01)
*B01D 3/28* (2006.01)
*C07C 67/04* (2006.01)
*C07C 67/38* (2006.01)
*C07C 67/54* (2006.01)

(52) U.S. Cl. ............... 203/29; 203/72; 203/75; 203/78; 203/87; 203/DIG. 9; 159/13.1; 159/27.1; 159/28.3; 159/43.1; 159/48.1; 159/49; 202/154; 202/155; 202/173; 202/186; 202/236; 202/259; 560/218; 560/233; 560/247

(58) Field of Classification Search ............ 203/29, 203/72–73, 74–75, 78, 80, 87, 90, 34–37, 203/DIG. 9, DIG. 21; 159/27.1, 28.3, 43.1, 159/49, 13.1–13.2; 202/172–173, 154–155, 202/236, 186, 259; 560/247, 218, 233; 562/600
See application file for complete search history.

(56) References Cited

U.S. PATENT DOCUMENTS

| | | | |
|---|---|---|---|
| 995,776 A * | 6/1911 | Dunn | 159/14 |
| 1,028,792 A * | 6/1912 | Sanborn | 159/17.1 |
| 2,392,255 A * | 1/1946 | McAndrews | 159/23 |
| 3,031,495 A | 4/1962 | Young et al. | |
| 3,037,052 A | 5/1962 | Bortnick | |
| 3,082,246 A | 3/1963 | Chafetz | |
| 3,087,962 A | 4/1963 | Bortnick | |
| 3,088,969 A | 5/1963 | Callahan et al. | |
| 3,172,905 A | 3/1965 | Eckert | |
| 3,620,283 A * | 11/1971 | Brown | 159/13.2 |
| 3,844,903 A | 10/1974 | Willersinn et al. | |
| 3,849,232 A * | 11/1974 | Kessler et al. | 159/13.2 |
| 4,054,485 A * | 10/1977 | Linder et al. | 159/6.2 |
| 4,094,734 A | 6/1978 | Henderson | |
| 5,004,043 A * | 4/1991 | Mucic et al. | 165/118 |
| 5,246,541 A * | 9/1993 | Ryham | 159/13.2 |
| 5,624,531 A * | 4/1997 | Knuutila et al. | 159/13.3 |
| 5,837,096 A * | 11/1998 | Fagerlind et al. | 159/13.3 |
| 6,066,232 A * | 5/2000 | Mohr et al. | 159/13.3 |
| 6,596,129 B1 * | 7/2003 | Yoneda et al. | 203/2 |
| 6,780,281 B1 * | 8/2004 | Elsner et al. | 159/2.1 |

FOREIGN PATENT DOCUMENTS

| | | |
|---|---|---|
| DE | 747 514 | 10/1944 |
| DE | 11 28 428 | 5/1962 |
| DE | 1 135 897 | 9/1962 |

| | | |
|---|---|---|
| DE | 12 49 857 | 9/1967 |
| DE | 21 64 767 | 7/1972 |
| DE | 31 05 399 | 10/1982 |
| EP | 024534 | 3/1981 |
| EP | 268999 | 6/1988 |
| JP | 60130546 | 7/1985 |

OTHER PUBLICATIONS

Houben-Weyl Methoden Der Organischen Chemie, vol. 8, pp. 534-536 1952.

\* cited by examiner

*Primary Examiner*—Virginia Manoharan
(74) *Attorney, Agent, or Firm*—Oblon, Spivak, McClelland, Maier & Neustadt, P.C.

(57) ABSTRACT

A tert-$C_4$–$C_8$-alkyl (meth)acrylate is prepared by reacting (meth)acrylic acid with an olefin of the formula

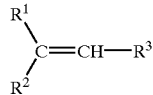

where
$R^1$ and $R^2$, which may be identical or different, are methyl or ethyl and $R^3$ is H, methyl or ethyl, in homogeneous phase in the presence of an acidic catalyst and isolating the tert-$C_4$–$C_8$-alkyl (meth)acrylate from the reaction mixture, by a process in which the catalyst is separated off as residue by a two-stage distillation of the reaction mixture and the tert-$C_4$–$C_8$-alkyl (meth)acrylate is isolated from the distillates.

Figure 1:
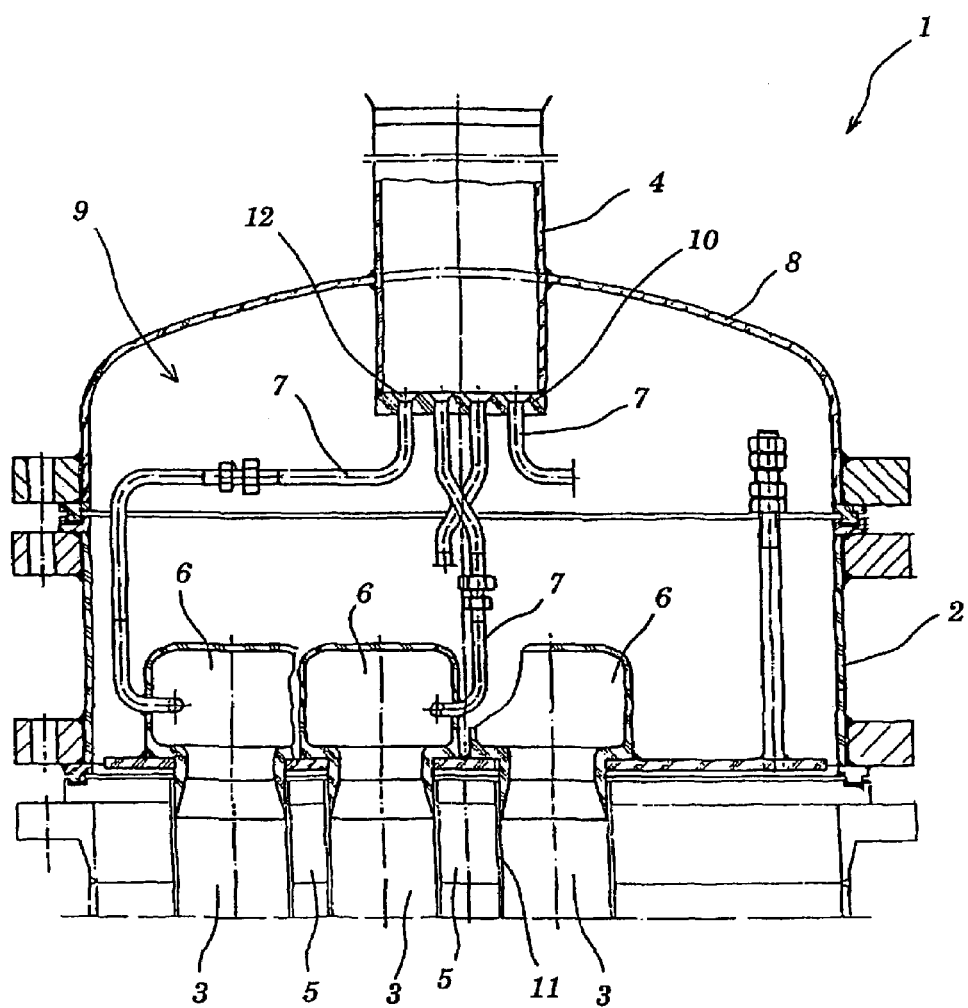

The novel process makes it possible to use acetic acid-containing (meth)acrylic acid. The danger of cleavage of the ester and of polymerization of (meth)acrylic compounds is reduced.

15 Claims, 1 Drawing Sheet

METHOD FOR PRODUCING TERTIARY C₄-C₈-ALKYL ESTERS OF (METH)ACRYLIC ACID

BACKGROUND OF THE INVENTION

1. Field of the Invention

The present invention relates to a process for the preparation of tert-$C_4$–$C_8$-alkyl esters of (meth)acrylic acid by reacting (meth)acrylic acid with an olefin of the formula

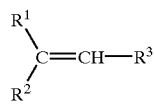

where
$R^1$ and $R^2$, which may be identical or different, are methyl or ethyl and $R^3$ is H, methyl or ethyl, in the presence of an acidic catalyst in homogeneous phase and isolating the ester from the reaction mixture.

2. Description of the Background

Tert-alkyl esters of (meth)acrylic acid are important starting materials for the preparation of polymers which are used, inter alia, as a component of coating dispersions, adhesives or coating resins. The preparation of tert-alkyl esters is carried out in general by an acid-catalyzed addition reaction of the corresponding carboxylic acids with isoolefins (Houben-Weyl, Methoden der Organischen Chemie, Vol. 8, 1952, page 534; U.S. Pat. Nos. 3,031,495 and 3,082,246). The catalysts used in the reaction mixture are soluble acids, for example mineral acids or alkanesulfonic or arylsulfonic acids (DE-A-12 49 857, U.S. Pat. No. 3,087,962, U.S. Pat. No. 3,088,969), or insoluble catalysts, such as acidic ion exchanger resins (U.S. Pat. No. 3,037,052, U.S. Pat. No. 3,031,495, DE-A-31 05 399, EP-A-268 999).

The reaction of the carboxylic acids with the isoolefins is carried out as a rule in conventional reaction containers or in columns (DE-A-11 28 428), the thorough mixing of the reaction mixture being effected by stirring or by the isoolefin stream passed in. Heat is removed in a conventional manner.

As a rule, the following difficulties arise during the preparation of tert-alkyl esters:
  oligomerization of the isoolefins
  polymerization of the (meth)acrylic acid or of the esters under thermal stress
  cleavage of the tert-alkyl esters under the action of heat and/or in the presence of traces of strong acids
  insufficient removal of the heat of reaction occurring in the strongly exothermic esterification reaction which may result in cleavage of the ester, oligomerization of the isoolefin and polymerization of the (meth)acrylic compounds.

In the prior art, numerous attempts have been made to reduce or to prevent the difficulties encountered. For example, the tendency of the isoolefins to oligomerize can be reduced by decreasing the reaction temperature (U.S. Pat. No. 3,172,905), by the presence of water (U.S. Pat. No. 3,088,969) and by partial neutralization of the catalyst (DE-A 31 05 399). However, these measures have the disadvantage that the reaction rate is reduced.

The formation of the isoolefin oligomers can also be reduced by using gaseous isoolefins (DE-A-11 35 897). However, the disadvantage here is the required vaporization of the liquid isoolefin and the handling of large amounts of gas.

Owing to the abovementioned difficulties, the isolation of the tert-alkyl ester from the reaction mixture is also particularly important. Frequently, the acidic catalyst is extracted and/or neutralized in order to prevent cleavage of the tert-ester (U.S. Pat. No. 3,172,905; U.S. Pat. No. 3,037,052; DE-A-11 28 428 and DE-A 11 35 897). However, this method causes environmental pollution and is uneconomical. Moreover, when amines are used for neutralizing the catalyst there is the danger that the polymerization of the (meth)acrylic acid and/or of the tert-ester will be promoted (cf JP 60 130 546). DE-A 12 49 857 proposes a mild distillation at from 30 to 80° C. and from 0.1 to 100 mbar for separating off the catalyst (sulfuric acid). The bottom product obtained is recycled to the reactor and the top product, a mixture of ester and diisoolefin, is further worked up. However, the fact that in this method the top product is nevertheless not completely free of catalyst is disadvantageous.

The strong tendency of (meth)acrylic compounds to polymerize, especially at relatively high temperatures, is known. Particularly in the purification by distillation these compounds are generally exposed to temperatures which can readily initiate an undesired polymerization. This results in soiling of the apparatuses, blockage of pipes and pumps and coating of column trays and heat exchanger surfaces. Cleaning of the plants is a complicated, expensive and environmentally polluting operation, and the availability of the plants is thus greatly reduced. It is important in this context that acetic acid is formed as a by-product in an amount of up to 1% by weight in the preparation of (meth)acrylic acid, for example by gas-phase oxidation of propene or acrolein or of isobutene or methacrolein over metal oxide catalysts. However, acetic acid is a troublesome component which has to be separated off before the (meth)acrylic acid is used. Owing to the small boiling point difference and the strong tendency of the (meth)acrylic acid to polymerize, however, removal of the acetic acid is difficult and expensive (U.S. Pat. No. 3,844,903 and DE-A 21 64 767), so that the use of substantially acetic acid-free (meth)acrylic acid is economically disadvantageous.

In order to avoid or reduce the polymer formation in (meth)acrylic compounds, as a rule polymerization inhibitors, for example phenothiazine, hydroquinone, hydroquinone monomethyl ether, p-nitrosophenol or tert-butylpyrocatechol or mixtures thereof, are used, if necessary with the simultaneous action of air (DE-A-11 35 897, DE-A-12 49 857, EP-A-0 24 534 and DE-A-29 31 553). Complete prevention of polymer formation is however not possible by the known methods.

SUMMARY OF THE INVENTION

It is an object of the present invention to provide a process for the preparation of tert-$C_4$–$C_8$-alkyl (meth)acrylate which permits improved removal of the catalyst in order to minimize the ester cleavage. It is a further object of the present invention to provide a process which permits the use of acetic acid-containing (meth)acrylic acid. It is a further object of the present invention to provide a process which gives the desired ester in high purity with very little polymer formation. In all cases, the process should be economical and technically simple.

We have found, surprisingly, that this object is achieved if the catalyst is separated by a two-stage distillation from the reaction mixture obtained by reacting (meth)acrylic acid with an olefin of the above formula, and the desired ester is isolated from the distillates.

The present invention therefore relates to a process for the preparation of tert-C$_4$–C$_8$-alkyl esters of (meth)acrylic acid by reacting (meth)acrylic acid with an olefin of the formula

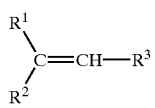

where

R$^1$ and R$^2$, which may be identical or different, are methyl or ethyl and R$^3$ is H, methyl or ethyl, in the homogeneous phase in the presence of an acidic catalyst and isolating the tert-alkyl ester from the reaction mixture by separating off the catalyst as a residue by a two-stage distillation of the reaction mixture and isolating the desired ester from the distillates.

DETAILED DESCRIPTION OF THE PREFERRED EMBODIMENTS

Usable isoolefins are for example isobutene, trimethylethene, 2-methyl-1-butene and 2-ethyl-1-butene, isobutene being particularly preferred.

1) Esterification

The reaction of the (meth)acrylic acid with the olefin of the above formula is carried out in a conventional manner. The manner in which this reaction is carried out has no effect on the novel process.

The process is carried out in general in the absence of a solvent and in liquid phase. The catalysts used are therefore those which are at least partially soluble in the reaction mixture. Usable catalysts are strong inorganic or organic acids, such as mineral acids, for example sulfuric acid, phosphoric acid and polyphosphoric acid, preferably sulfuric acid, or sulfonic acids, such as p-toluenesulfonic, benzenesulfonic, dodecylbenzenesulfonic and methanesulfonic acid.

The amount of catalyst is in general from about 1 to 10, preferably from 2 to 5, % by weight, based on (meth)acrylic acid.

The olefin may be used in gaseous and/or liquid form. The (meth)acrylic acid used may contain acetic acid in an amount of up to 1% by weight.

In general, the (meth)acrylic acid used has the following composition:

| (Meth)acrylic acid | from 99.0 | to 99.9% by weight |
| --- | --- | --- |
| Acetic acid | from 0.05 | to 0.5% by weight |
| Propionic acid | from 0.02 | to 0.4% by weight |
| Water | from 0.01 | to 0.1% by weight |

The reactants may be used in stoichiometric amounts. In general, however, one of the reactants is used in excess, preferably the (meth)acrylic acid, and in particular an excess of up to 50 mol %.

The reaction temperature is in general from 20 to 40° C. and the reaction time is usually from 1 to 6 hours. The pressure is not critical; reduced, superatmospheric or, preferably, ambient pressure or slightly superatmospheric pressure (100-300 mbar) may be used.

The reaction is carried out in general in the presence of an inhibitor which inhibits the polymerization of the (meth) acrylic acid or of the ester. Particularly suitable inhibitors are hydroquinone, hydroquinone monomethyl ether, p-benzoquinone, p-nitrosophenol, phenothiazine, N-oxyl compounds, e.g. 4-hydroxy-2,2,6,6-tetramethyl-1-oxylpiperidine, and methylene blue. The inhibitors are used in general in amounts of from about 200 to 2000 ppm, based on the weight of the starting materials (meth)acrylic acid and isoolefin.

The process can be carried out continuously or batchwise in conventional reactors. In the case of isobutene, the reaction mixture obtained generally has the following composition:

| tert-butyl (meth)acrylate | from 50 | to 90% by weight |
| --- | --- | --- |
| (meth)acrylic acid | from 10 | to 30% by weight |
| tert-butanol | from 0.1 | to 1% by weight |
| tert-butyl acetate | from 0.1 | to 1% by weight |
| diisobutene | from 0.05 | to 1% by weight |
| acidic catalyst | from 1 | to 5% by weight |
| polymerization inhibitor | from 0.05 | to 0.2% by weight |

2) Removal of Catalyst

The reaction mixture is then separated in a two-stage distillation. The distillation can be effected at elevated temperatures and at reduced pressure. The conditions depend on the product desired in each case. They are chosen as a rule so that the temperature is from about 50 to 150° C. The pressure is then chosen according to the isoolefin used. However, the pressure is established so that the distillation takes place rapidly and gently.

The stepwise distillation is carried out so that from 40 to 95, preferably from 60 to 90% by weight of the desired ester are distilled off in the first stage. In addition to the desired ester and (meth)acrylic acid, the distillate contains the low-boiling components, such as tert-butanol, tert-butyl acetate and diisobutene (when isobutene is used). The bottom product obtained in the first distillation substantially comprises the remaining desired ester, (meth)acrylic acid and high-boiling components, for example polymeric (meth) acrylic compounds. From 10 to 100% by weight of the bottom product are fed to the second distillation stage. If only a part of the bottom product is fed to the second distillation stage, the remainder of the bottom product is recycled to the reactor. In the second distillation stage, the remaining desired ester and the main amount of (meth) acrylic acid (up to about 90% by weight) are distilled off. The distillates of both stages are expediently combined or condensed together.

The bottom product of the second distillation stage substantially comprises the acidic catalyst, the remaining (meth) acrylic acid and high-boiling components, in particular polymeric (meth)acrylic compounds. In the two-stage distillation, the reaction mixture is thus separated into a distillate which substantially comprises the desired ester, (meth) acrylic acid and the stated low-boiling components and into a residue (bottom product) which substantially comprises the acidic catalyst, (meth)acrylic acid and the stated high-boiling components. The distillate contains in general <20 ppm, particularly <10 ppm, of catalyst.

From 10 to 100, preferably from 30 to 80, % by weight of the second bottom product are removed and the remainder is recycled to the reactor.

Both distillation stages can be carried out in conventional apparatuses. Preferably, however, apparatuses which permit rapid distillation, for example film evaporators, are used. Suitable film evaporators are known to a person skilled in the art (cf. for example Ullmann's Encyclopedia of Industrial Chemistry, 5th Ed., Vol. B3, 2-21 to 2-24 and 3-1 to 3-25, 1988. Falling-film or downflow evaporators are preferably used in the first distillation stage and thin-film evaporators in the second stage.

It has proven particularly preferable to use, in the first distillation stage, a modified falling-film evaporator which is described in more detail below and in which the evaporator tubes are closed at the top. Each individual evaporator tube is equipped with a separate feed for introducing reaction mixture into the closed top region of the evaporator tube. For example, the reaction mixture is fed via a tube which opens into a chamber above the relevant evaporator tube. With the aid of this modified falling-film evaporator, the polymer formation in the top part of the evaporator is prevented and obstruction or blockage of the evaporator tubes is avoided.

The vapors can be condensed in the usual manner, for example in condensers of conventional design. Preferably, two condensers connected in series, in particular plate-type or tube-bundle condensers, are used, the second condenser being operated at the lower cooling temperature. In general, the temperature difference is from about 30 to 50° C., the cooling temperature of the first condenser being from about 10 to 25° C. In this way, rapid distillation and condensation are permitted and polymer formation is suppressed. In order to reduce the polymer formation even further, an inhibitor dissolved in the desired ester is introduced into the second condenser. The inhibitor used is preferably a mixture of nitrosophenol and phenothiazine, which is expediently introduced as a solution of from 0.5 to 0.7 kg of p-nitrosophenol and from 0.5 to 1.5 kg of phenothiazine in 100 l of desired ester, preferably in the top region of a vertically arranged second condenser. The inhibitor solution is applied in an amount such that the inhibitor concentration in the combined condensates is roughly in the range of from 100 to 500 ppm. The inhibitor is introduced in the usual manner, preferably by spraying in the inhibitor solution. For reducing the polymer formation, it has moreover proven advantageous to introduce, in particular to spray in, at least ten times the amount of distillate (crude ester) into the first condenser, preferably in the top region of a vertically arranged condenser.

3) Separating off low boilers

In order to isolate the desired ester from the combined distillates from the catalyst removal, the distillate is separated in a conventional distillation unit comprising evaporator, column and condenser into a top product and a bottom product. The distillation temperature (bottom temperature) is in general from 30 to 60° C. The pressure is accordingly chosen depending on the product.

The top product contains the low-boiling components, such as tert-butyl acetate, tert-butanol and diisobutene. It may also contain up to 5% by weight, based on the top product, of desired ester. The bottom product substantially comprises the desired ester and (meth)acrylic acid.

Suitable columns are conventional columns having beds or stacked packings or having bubble trays, valve trays or sieve trays. However, a tray column having from 30 to 50 dual-flow trays is preferably used. The feed to the distillation column is in general in the middle region.

According to one variant, a small amount (from 0.01 to 0.1% by weight, based on the distillate of the catalyst removal) of a basic compound is added to the feed to the low boiler removal. Suitable basic compounds are, for example, alkali metal or alkaline earth metal compounds, for example sodium, potassium or calcium hydroxide, carbonate or bicarbonate, or primary, secondary and in particular tertiary amines. The substituents on the nitrogen of the amines may be $C_1$–$C_{20}$-alkyl, aryl or $C_1$–$C_{12}$-alkylaryl groups and may be unsubstituted or substituted by hydroxyl. Polyamines, such as di- and triamines may also be used. Triethylamine, tributylamine, tri-2-ethylhexylamine, N,N-dimethyldodecylamine, N,N-dimethylaniline, N,N-dimethylbenzylamine, N,N,N',N'-tetramethyl-1,3-propanediamine, triethanolamine, diethylethanolamine, n-butyldiethanolamine or methyldiisopropanolamine is preferably used.

By adding a base, the cleavage of the tert-alkyl ester is substantially prevented. Although JP-A-60 130 456 discloses that the addition of amines reduces the stability of (meth)acrylic compounds, it has surprisingly been found that no polymer formation takes place when a base is added, so that the operation of the plant is not adversely affected by coating of heat exchanger surfaces, or deposits on column trays and/or in pipes and containers.

The condensation of the low-boiling components is effected in a conventional manner. Preferably the condensation is effected in two condensers connected in series, for example tube-bundle condensers. The cooling temperature of the second condenser is about 30 to 50° C. lower, and the first condenser is operated at a cooling temperature of from about 10 to 25° C. The condensates are combined and are partly used as column reflux. The remainder of the condensate is removed. In order to prevent polymer formation in the first condenser and in the column, a solution of an inhibitor in desired ester is applied to the first condenser. Preferably, a solution of from 0.5 to 1.5 kg of phenothiazine and from 0.3 to 0.7 kg of p-nitrosophenol in 100 l of desired ester is used. The inhibitor solution is applied in an amount such that the inhibitor concentration is roughly in the range from 100 to 500 ppm.

4) Purification by Distillation

The desired ester is isolated in a purity of at least 99.5% from the bottom product of a low boiler distillation in a distillation unit of conventional design (evaporator, column and condenser). The resulting bottom product contains at least 70% by weight of (meth)acrylic acid and is once again recycled to the reactor. The distillation temperature is in general from 40 to 80° C. The pressure is chosen according to the ester to be distilled.

The purification by distillation is effected using a conventional tray column, for example a column having from 30 to 50 dual-flow trays and a feed in the middle region of the column. The pure desired ester is isolated via the top. The condensation of the desired ester is preferably effected in two condensers arranged in series, particularly in tube-bundle condensers. The temperature of the coolant of the second condenser is from about 30 to 50° C. lower than that of the first condenser, in which the coolant has a temperature of from about 10 to 25° C. The combined condensates are used partly as column reflux and partly for stabilizing the top of the column and the first condenser, i.e. for avoiding polymerization in the top of the column and in the first condenser. The remainder (about 10% by weight) of the desired ester is removed. In order to avoid polymerization in the second condenser, a solution of an inhibitor in desired ester is introduced. Preferably, a solution of from 0.5 to 1% by weight of hydroquinone monomethyl ester is used, the amount of inhibitor introduced being chosen so that the inhibitor content of the combined condensates is from 10 to 20 ppm. In order to avoid polymerization in the first condenser, a part (about 5 to 10 times the amount of desired ester removed) of the combined, stabilized condensates is introduced into the vapor tube. The introduction of the condensates is preferably effected by spraying into the vapor tube in the direction opposite to that of the gas stream, the nozzle expediently being installed in the vapor tube in the region of the condenser inlet.

The polymerization in the column is suppressed on the one hand by the reflux of the condensate, which contains from 10 to 20 ppm of inhibitor. On the other hand, a solution of a further inhibitor in desired ester is additionally applied to a tray in the upper column region. Preferably, a solution of from 0.5 to 1.5 kg of phenothiazine and from 0.3 to 0.7 kg of p-nitrosophenol in 100 l of desired ester is used, the amount being such that the inhibitor content is from 50 to 500 ppm in the rectification section. Furthermore, a solution of from 15 to 30 g of hydroquinone monomethyl ether (MEHQ) in 100 l of desired ester is introduced into the top of the column. This is expediently done by spraying in via a nozzle installed centrally in the vapor tube outlet. If desired, oxygen-containing gas, e.g. air, can be blown into the distillation unit for further stabilization. As a result of these measures, it is possible to prevent polymer formation in the condensers, in the vapor tubes and in the column.

The ester obtained is of high purity and, when isobutene is used, generally has the following composition:

| | | |
|---|---|---|
| tert-butyl (meth)acrylate | from 99.5 | to 99.9% by weight |
| tert-butyl acetate | from 0.001 | to 0.01% by weight |
| tert-butyl propionate | from 0.02 | to 0.03% by weight |
| tert-butanol | from 0.001 | to 0.01% by weight |
| (meth)acrylic acid | from 0.005 | to 0.02% by weight |
| hydroquinone monomethyl ether | from 0.001 | to 0.002% by weight |

The novel process has the following advantages over the prior art:
- Acetic acid-containing (meth)acrylic acid may be used. The difficult and technically complicated removal of acetic acid by distillation can therefore be omitted and surprisingly a tert-alkyl ester of high purity is nevertheless obtained.
- By the two-stage separation of the desired ester from the catalyst, the residual content of catalyst is surprisingly considerably reduced. The cleavage of the desired ester is thus substantially reduced.
- A part of the catalyst-containing residue is removed and is replaced by fresh catalyst. The run-time of the production plant can thus surprisingly be substantially increased.
- By the two-stage condensation of the vapors, polymerization of the (meth)acrylic compounds can surprisingly be substantially prevented and long run-times can be achieved.
- This effect is further reinforced by the special stabilization of column and condenser in the removal of low boilers and the purification by distillation.

The present invention also relates to an apparatus for carrying out the novel process. It comprises a falling-film evaporator having a cylindrical jacket, a multiplicity of evaporation tubes arranged in the jacket, means for feeding in the liquid to be vaporized and means for heating the evaporation tube, wherein, in the falling-film evaporator, at least one of the evaporation tubes has a closed top region into which a feed pipe for the liquid to be vaporized opens, the feed pipe communicating with the means for feeding in the liquid to be vaporized.

A multiplicity of evaporation tubes which are parallel to the jacket surface are arranged in the cylindrical jacket of the falling-film evaporator. In general, the jacket is closed in the upper region by a generally dome-shaped cover to form a space which can at least partly hold means for feeding in the liquid to be vaporized and the feed pipes to the evaporation tubes.

The means for feeding in the liquid to be vaporized is in general a container or a tube having an larger diameter than the pipes. Both the container and the tube have a base plate or end plate with means for connecting the feed pipes. Expediently, these are flanges, holes, threads, etc. in the base plate, to which the feed pipes can be connected. The feed pipes may also be welded to the base plate. The means for feeding in the liquid to be vaporized are preferably at least partly arranged inside the space enclosed by the dome-shaped cover at the top of the falling-film evaporator.

The feed pipes for feeding the liquid to be evaporated into the evaporation tubes are generally in the form of a tube and extend from the bottom of the means for feeding the liquid to be vaporized to the evaporation tubes.

The evaporation tubes have a closed top region. This can be effected in various ways, for example by means of a plate at the upper end of the evaporation tubes. Preferably, however, the closed top region is in the form of a chamber which expediently connects to the end of the evaporation tube. The diameter of the chamber may be greater than the diameter of the respective tube. The feed pipes for the liquid to be vaporized project, preferably laterally, into the closed head region.

Moreover, the falling film evaporator has means for heating the evaporation tubes, as usually used in this field. For example, a liquid heat-transfer medium can flow around the evaporation tubes. Moreover, the falling-film evaporator has conventional measuring and control means for carrying out the process.

The falling-film evaporator is explained below with reference to FIG. 1.

FIG. 1 shows a schematic diagram of a section through the top region of a preferred embodiment of a novel falling-film evaporator.

The falling-film evaporator 1 is bounded by a jacket 2 in cylindrical form. The upper end of the cylinder formed by the jacket has a cover 8. The jacket surrounds a multiplicity of evaporation tubes 3 which are arranged substantially parallel to the jacket surface. The evaporation tubes 3 are arranged in such a way that their top end is below the top end of the jacket, so that a space 9 enclosed by the jacket 2 and by the cover 8 is formed at the top of the falling-film evaporator. A container 4 for feeding in the liquid to be vaporized projects into the space 9.

The evaporation tubes 3 have a closed top region 6 which is in the form of a chamber and connects to the end of the cylindrical evaporation tubes 3. That end of the container 4 which projects into the space 9 is closed by a base 10 which has holes 12 for the connection of a plurality of feed pipes 7. The feed pipes 7 lead from the base 10 into the closed head region 6 of the evaporation tubes 3.

When the falling-film evaporator is used, the container 4 is fed with the liquid to be vaporized. The liquid is fed via the feed pipes 7 into the closed head region 6 at a rate corresponding to the rate of vaporization. The vaporization of the liquid, condensation of the vapors, recovery and discharge of the residue, etc. are then effected in a conventional manner, i.e. the liquid to be vaporized flows downward over the inner surfaces of those walls 11 of the evaporation tubes 3 which are heated by a heat-transfer medium 5, the more readily volatile components of the liquid vaporizing.

The novel falling-film evaporator has the advantage that the vaporization takes place under very mild conditions so that polymer formation is reduced in the novel process.

The examples which follow illustrate the invention without restricting it. All stated percentages are by weight.

EXAMPLE 1

Preparation of Tert-Butyl Acrylate

The starting material used was an acrylic acid having substantially the following composition:

| | |
|---|---|
| acrylic acid | 99.5% |
| acetic acid | 0.2% |
| propionic acid | 0.03% |
| diacrylic acid | 0.1% |
| water | 0.1% |
| hydroquinone monomethyl ether (MEHQ) | 0.02% |

The esterification of acrylic acid of the above composition with isobutene in the presence of sulfuric acid and phenothiazine was carried out according to example 2 of DE 12 49 857 and gave an esterification mixture which contained, inter alia, the following components:

| | |
|---|---|
| tert-butyl acrylate | 64.0% |
| tert-butyl acetate | 0.2% |
| tert-butanol | 1.6% |
| acrylic acid | 24.1% |
| diisobutene | 1.2% |
| sulfuric acid | 1.0% |
| tert-butylsulfuric acid | 5.3% |
| phenothiazine | 0.1% |

The esterification mixture was fed to a tube-bundle evaporator (70° C., 70 mbar) and 50% of the feed were distilled off. The resulting residue was then passed via a thin-film evaporator (Sambay; 80° C., 60 mbar), 13% of the original feed being separated off as distillate. A part (3%) of the bottom product of the Sambay distillation was removed and the remainder was recycled to the synthesis. The vapors formed in the distillation were condensed together in two tube-bundle condensers connected in series, the first being cooled with cooling water (20° C.) and the second with brine (−20° C.). The resulting condensates were combined. The tubes of the brine condenser were sprayed at the top with a solution (15 l/h) of 0.8% phenothiazine and 0.4% p-nitrosophenol in tert-butyl acrylate. At the top of the first condenser, about 16 m³/h of recycled condensate were sprayed on. According to the acid-base titration the combined condensates contained 19.8% acrylic acid and <10 ppm sulfuric acid.

For separating off low boilers, the combined condensates were fed to a distillation unit which consisted of an external natural circulation evaporator, a distillation column having 40 dual-flow trays (feed onto tray 22) and two condensers arranged in series, the first condenser being operated with cooling water (20° C.) and the second one with brine (−20° C.). The components having a boiling point lower than that of tert-butyl acrylate, mainly tert-butyl acetate, diisobutene and tert-butanol, were separated off via the top of the column (38° C., 115 mbar) and were condensed (38 l/h), the first condenser being fed with a solution (15 l/h) of 0.8% phenothiazine and 0.4% p-nitrosophenol in tert-butyl acrylate.

The combined low boiler condensates were partly discharged (38 l/h) and partly applied as reflux (1250 l/h) to the uppermost tray of the column.

The resulting bottom product, mainly comprising tert-butyl acrylate and acrylic acid, was separated in a further distillation unit into a top product, i.e. tert-butyl acrylate, and a bottom product, mainly acrylic acid, which was recycled to the synthesis (purification by distillation).

The distillation unit consisted of an external tube-bundle evaporator, a column having 40 dual-flow trays (feed onto tray 18) and two condensers arranged in series, the first being operated with cooling water (20° C.) and the second with brine (−20° C.).

The combined condensates were partly discharged (1200 l/h), partly applied as reflux (about 1.1 m³/h) to the uppermost tray of the column and partly (12.5 m³/h) sprayed into the vapor tube of the first condenser, in the direction opposite to that of the gas flow. The column was moreover stabilized by a solution (15 l/h) of 0.8% of phenothiazine and 0.4% of p-nitrosophenol in tert-butyl acrylate, with the solution being fed to the upper column region (tray 38).

In addition, a mixture of 300 l of reflux and 6 l of a solution of 1.2% of hydroquinone monomethyl ether (MEHQ) in tert-butyl acrylate was fed per hour into the top column via a nozzle which was arranged centrally in the inlet into the vapor tube. The second condenser was fed with a solution (1.7 l/h) of 1.2% of MEHQ in tert-butyl acrylate.

The tert-butyl acrylate isolated contained 150 ppm of acrylic acid and had a purity of 99.94%.

The exit gases occurring in the individual distillation steps, substantially isobutene, were combined and recycled to the synthesis via a compressor.

EXAMPLE 2

The catalyst removal described in two stages in Example 1 was carried out in one stage in the thin-film evaporator at 80° C. and 60 mbar. According to the acid-based titration, the condensate contained 100 ppm of sulfuric acid.

EXAMPLE 3

Isobutene-free tert-butyl acrylate (5 ml) to which various amounts of sulfuric acid had been added were stored in 20 ml ampoules for 2 hours at 60° C., and the content of isobutene in the gas phase was then determined by gas chromatography.

| Amount of sulfuric acid | Isobutene content |
|---|---|
| 0 ppm | <5 ppm |
| 20 ppm | 27 ppm |
| 100 ppm | 180 ppm |
| 320 ppm | 1370 ppm |

The experiments clearly show that, owing to the lower sulfuric acid content, the ester cleavage in the novel process is considerably less than in the one-stage catalyst removal according to the prior art.

EXAMPLE 4

The procedure was analogous to that of Example 2. 50 ppm of tributylamine were added continuously to that part of the combined condensates from the catalyst removal which was fed to the low boiler removal and contained 10 ppm of sulfuric acid. The tert-butyl acrylate obtained in the purification by distillation had a purity of 99.95% and contained less than 50 ppm of isobutene. No adverse effect (e.g. polymer formation) on the distillative working-up due to the amine addition was observed in the course of an operating time of 20 days.

What is claimed is:

1. A process for the production of a tert-$C_4$–$C_8$-alkyl (meth)acrylate by reacting (meth)acrylic acid with an olefin of the formula:

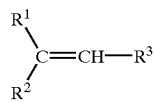

wherein $R^1$ and $R^2$, which are identical or different, are methyl or ethyl and $R^3$ is H, methyl or ethyl, in the homogeneous phase in the presence of an acidic catalyst, thereby obtaining a reaction mixture containing tert-$C_4$–$C_8$-alkyl (rneth)acrylate produced, and then isolating the tert-$C_4$–$C_8$-alkyl (meth)acrylate by a distillation process comprising:

distilling said reaction mixture in a first stage, thereby obtaining a distillate containing tert-$C_4$–$C_8$-alkyl (meth)acrylate which is isolated from the remaining components of the distillate in an amount of 40 to 95% by wt of the total tert-$C_4$–$C_8$-alkyl (meth)acrylate produced and obtaining a residue; and distilling from 10 to 100% by wt of said residue in a second stage, thereby obtaining a distillate of the remainder of the tert-$C_4$–$C_8$-alkyl (meth)acrylate and much of the unconverted (meth)acrylic acid in said reaction mixture and a residue, the catalyst of the esterification process being separated by the two stage distillation as a residue material.

2. The process as claimed in claim 1, wherein the distillation of the first stage is conducted in a falling-film evaporator that contains a plurality of evaporator tubes, each evaporator tube having a closed top region and each tube being separately fed with said reaction mixture.

3. The process as claimed in claim 1, wherein each distillate that is obtained in the distillation process is condensed in two condensers that are connected in series.

4. The process as claimed in claim 1, wherein the distillates from each of the two stages of distillation are combined and then are subjected to distillation in a first column, thereby separating a top product that comprises low boiling material and a bottom product comprising said tert-$C_4$–$C_8$-alkyl (meth)acrylate and (meth)acrylic acid.

5. The process as claimed in claim 4, wherein from 0.01 to 0.1% by wt of a basic compound is added to the combined distillate material before distillation in the column to effect formation of said top product.

6. The process as claimed in claim 4, wherein said top product is condensed in two condensers connected in series and a solution of a polymerization inhibitor in tert-$C_4$–$C_8$-alkyl (meth)acrylate is introduced into the first of the two condensers.

7. The process as claimed in claim 4, wherein said bottom product is subjected to distillation in a second column, whereby tert-$C_4$–$C_8$-alkyl (meth)acrylate is obtained as a distillate at the top of the column.

8. The process as claimed in claim 7, wherein a solution of a polymerization inhibitor in tert-$C_4$–$C_8$-alkyl (meth)acrylate is sprayed onto a tray in the upper region of said column and a solution of hydroquinone monomethyl ether in tert-$C_4$–$C_8$-alkyl (meth)acrylate is sprayed into the top of said column.

9. The process as claimed in claim 1, wherein said olefin is isobutene, trimethylethene, 2-methyl-1-butene or 2-ethyl-1-butene.

10. The process as claimed in claim 9, wherein isobutene is said olefin and tert-butyl (meth)acrylate is obtained as the tert-$C_4$–$C_8$-alkyl (meth)acrylate product.

11. The process as claimed in claim 1, wherein said acid catalyst is sulfuric acid, phosphoric acid, polyphosphoric acid, p-toluenesulfonic acid, benzenesulfonic acid, dodecylbenzenesulfonic acid or methanesul fonic acid.

12. The process as claimed in claim 1, wherein said acid catalyst is present in the reaction mixture in an amount of 1 to 10% by wt.

13. A falling-film evaporator, comprising:

a cylindrical jacket, a multiplicity of evaporation tubes, wherein an end of each tube has a closed top region and with each tube arranged so that the closed top regions are enclosed in the jacket, means for feeding a liquid to be vaporized into the evaporator projecting through said jacket, said feeding means in the form of a container or tube and said container or said tube having a base which has holes for connection with each of a plurality of feed pipes for supplying said liquid to be vaporized to each of the evaporation tubes, a feed pipe attached to each of said closed ends and in open communication with each of the closed top regions, and each feed pipe in open conin-lunication with the base of said feeding means, thereby providing passage of a liquid to be vaporized from said feeding means to each closed top, and means for heating the evaporation tubes.

14. The falling-film evaporator as claimed in claim 13, wherein each of said closed tops is in the form of a chamber which connects to the upper end of each evaporation tube.

15. The falling-film evaporator as claimed in claim 13, wherein the feeding means projects into the evaporator through the top portion of the jacket.

* * * * *